US009101646B2

(12) United States Patent
Gleave et al.

(10) Patent No.: US 9,101,646 B2
(45) Date of Patent: *Aug. 11, 2015

(54) BISPECIFIC ANTISENSE OLIGONUCLEOTIDES THAT INHIBIT IGFBP-2 AND IGFBP-5 AND METHODS OF USING SAME

(75) Inventors: Martin Gleave, Vancouver (CA); Maxim Signaevsky, Vancouver (CA)

(73) Assignee: The University of British Columbia, Vancouver (CA)

(*) Notice: Subject to any disclaimer, the term of this patent is extended or adjusted under 35 U.S.C. 154(b) by 862 days.

This patent is subject to a terminal disclaimer.

(21) Appl. No.: 12/752,581

(22) Filed: Apr. 1, 2010

(65) Prior Publication Data
US 2010/0267808 A1 Oct. 21, 2010

Related U.S. Application Data

(62) Division of application No. 12/109,747, filed on Apr. 25, 2008, now Pat. No. 7,928,082, which is a division of application No. 10/346,493, filed on Jan. 17, 2003, now abandoned.

(60) Provisional application No. 60/350,046, filed on Jan. 17, 2002.

(51) Int. Cl.
C07H 21/04 (2006.01)
A61K 31/713 (2006.01)
C12N 15/113 (2010.01)
A61K 38/00 (2006.01)

(52) U.S. Cl.
CPC ............ *A61K 31/713* (2013.01); *C12N 15/113* (2013.01); *A61K 38/00* (2013.01); *C07K 2319/00* (2013.01); *C12N 2310/11* (2013.01); *C12N 2310/3519* (2013.01); *C12N 2310/51* (2013.01)

(58) Field of Classification Search
None
See application file for complete search history.

(56) References Cited

U.S. PATENT DOCUMENTS

| | | | | |
|---|---|---|---|---|
| 5,417,978 A * | 5/1995 | Tari et al. | | 424/450 |
| 5,646,042 A | 7/1997 | Stinchcomb et al. | | |
| 5,855,911 A * | 1/1999 | Lopez-Berestein et al. | | 424/450 |
| 5,929,040 A | 7/1999 | Werther et al. | | |
| 5,998,148 A | 12/1999 | Bennett et al. | | |
| 6,210,892 B1 | 4/2001 | Bennett et al. | | |
| 6,284,741 B1 | 9/2001 | Werther et al. | | |
| 6,310,047 B1 * | 10/2001 | Farrell et al. | | 514/44 A |
| 7,297,684 B1 | 11/2007 | Gleave et al. | | |
| 7,973,017 B2 * | 7/2011 | Gleave | | 514/44 A |
| 8,252,765 B2 * | 8/2012 | Gleave | | 514/44 A |
| 8,541,390 B2 * | 9/2013 | Gleave | | 514/44 A |
| 2003/0087857 A1 | 5/2003 | Freier | | |

FOREIGN PATENT DOCUMENTS

| | | |
|---|---|---|
| WO | 00/69454 | 11/2000 |
| WO | 00/78341 | 12/2000 |
| WO | 01/05435 | 1/2001 |
| WO | 02/22642 | 3/2002 |

OTHER PUBLICATIONS

Blast sdequence alignments for instant SEQ ID No. 5, retrieved from http://blast.ncbi.nlm.nih.gov/Blast.cgi#alnHdr_551848515 on Mar. 27, 2014.*
Agrawal et al., "Antisense Therapeutics: Is it as simple as complementary base recognition", Molecular Medicine Today, 2000, pp. 72-81, vol. 6, Publisher: Elsevier Science Ltd.
Andress et al., "Human Osteoblast-derived Insulin-like Growth Factor (IGF) Binding Protein-5 Stimulates Osteoblast Mitogenesis and Potentiates IGF Action", The Journal of Biological Chemistry, Nov. 1992, pp. 22467-22472, vol. 267, No. 31.
Angelloz-Nicoud et al., Autocrine Regulation of Cell Proliferation by the Insulin-Like Growth Factor (IGF) and IGF Binding Protein-3 Protease System in a Human Prostate Carcinoma Cell Line (PC-3), Endocrinology, 1995, pp. 5485-5492, vol. 136, No. 12.
Boudon et al., "Secretion of Insulin-Like Growth Factors and Their Binding Proteins by Human Normal and Hyerplastic Prostatic Cells in Primary Culture", Journal of Clinical Endocrinology and Metabolism, Feb. 1, 1996, pp. 612-617, vol. 81, No. 2.
Branch, Andrea D., "A good antisense molecule is hard to find", TIBS, 1998, pp. 45-50, Publisher: Elsevier Science Ltd.
Crooke et al., "Basic Principles of Antisense Therapeutics, Antisense Research and Application", 2004, pp. 1-50, Publisher: Springer.
Cucco, et al., "In Vitro and in Vivo Reversal of Multidrug Resistance in a Human Leukemia-resistant Cell Line by mdr1 Antisense Oligodeoxynucleotides1", Cancer Research, Oct. 1, 1996, pp. 4332-4337, vol. 56.
Damon et al., "Overexpression of an Inhibitory Insulin-Like Growth Factor Binding Protein (IGFBP), IGFBP-4, Delays Onset of Prostate?Tumor Formation", Endocrinology, 1998, pp. 3456-3464, vol. 139, No. 8.
Elgin et al., "An insulin-like growth factor (IGF) binding protein enhances the biologic response to IG-1,", Proc. Natl. Acad. Sci. USA, May 1987, pp. 3254-3258, vol. 84.
Figueroa et al., "Differential Expression of Insulin-Like Growth Factor Binding Proteins in High Versus Low Gleason Score Prostate Cancer", The Journal of Urology, Apr. 1998, pp. 1379-1383, vol. 159(4).
Huynh et al., "Estradiol and Antiestrogens Regulate a Growth Inhibitory Insulin-like Growth Factor Binding Protein 3 Autocrine Loop in Human Breast Cancer Cells", The Journal of Biological Chemistry, Jan. 1996, pp. 1016-1021, vol. 271, No. 2.
Jansen et al., "bcl-2 antisense therapy chemosensitizes human melanoma in SCID mice", Nature Medicine, Feb. 1998, pp. 232-234, vol. 4, No. 2.

(Continued)

*Primary Examiner* — Richard Schnizer
(74) *Attorney, Agent, or Firm* — Larson & Anderson, LLC

(57) ABSTRACT

Bispecific antisense oligonucleotides which consist essentially of a sequence of bases that is complementary to portions of both the gene encoding human IGFBP-2 and the gene encoding human IGFBP-5 are useful in as antisense therapeutics in the treatment of endocrine-regulated cancers.

9 Claims, 11 Drawing Sheets

(56) References Cited

OTHER PUBLICATIONS

Jen et al., "Suppression of Gene Expression by Targeted Disruption of Messenger RNA: Available Options and Current Strategies", Stem Cells 2000, 2000, pp. 307-319, vol. 18.

Monia et al., "Antitumor activity of a phosphorothioate antisense oligodeoxynucleotide targeted against C-raf kinase", Nature Medicine, Jun. 1996, pp. 668-675, vol. 2, No. 6.

Nickerson et al., "Castration-induced apoptosis in the rat ventral prostate is associated with increased expression of genes encoding insulin-like growth factor binding proteins 2,3,5, and 5", Endocrinology, 1998, pp. 807-810, vol. 139, No. 2.

Oh et al., "Management of Hormone Refractory Prostate Cancer: Current Standards and Future Prospects", The Journal of Urology, Oct. 1998, pp. 1220-1229, vol. 160(4).

Oh et al., "Insulin-like Growth Factor (IGF)-independent Action of IGF-binding Protein-3 in Hs578T Human Breast Cancer Cells", The Journal of Biological Chemistry, 1993, pp. 14964-14971, vol. 268, No. 20.

Opalinska et al., "Nucleic-acid therapeutics: Basic principles and recent applications", Nature Reviews, 2002, pp. 503-514, vol. 1.

Rajaram et al., "Insulin-Like Growth Factor-Binding Proteins in Serum and Other Biological Fluids: Regulation and Functions", Endocrine Reviews, 1997, pp. 801-831, vol. 18(6).

Ziegler et al, "Induction of Apoptosis in Small-Cell Lung Cancer Cells by an Antisense Oligodeoxynucleotide Targeting the Bcl-2 Coding Sequence", Journal of the National Cancer Institute, Jul. 16, 1997, pp. 1027-1036, vol. 89, No. 14.

Akkiprik et al., "Multifunctional roles of insulin-like growth factor binding protein 5 in breast cancer", Breast Cancer Res. 10:202, 2008, pp. 1-14.

Beattie et al., "Insulin-like growth factor-binding protein-5 (IGFBP-5): a critical member of the IGF axis", Biochem. J., 2006, pp. 1-19, vol. 395.

Butt et al., "Insulin-like Growth Factor-binding Protein-5 Inhibits the Growth of Human Breast Cancer Cells in Vitro and in Vivo", The Journal of Biological Chemistry, 2003, pp. 29676-29685, vol. 278, No. 32.

Hung et al., "Insulin-like growth factor binding protein-5 (IGFBP-5) suppresses the tumourigenesis of head and neck squamous cell carcinoma", Journal of Pathology, 2008, pp. 368-376, vol. 214.

Huynh et al., "A Role for Insulin-like Growth Factor Binding Protein 5 in the Antiproliferative Action of the Antiestrogen ICI 182780", Cell Growth & Differentiation, 1996, pp. 1501-1506, vol. 7.

Miyake et al., "Castration-induced Up-Regulation of Insulin-like Growth Factor Binding Protein-5 Potentiates Insulin-like Growth Factor-I Activity and Accelerates Progression to Androgen Independence in Prostate Cancer Models", Cancer Research, 2000, pp. 3058-3064, vol. 60.

Miyake et al., "Novel therapeutic strategy for advanced prostate cancer using antisense oligodeoxynucleotides targeting anti-apoptotic genes upregulated after androgen withdrawal to delay androgen-independent progression and enhance chemosensitivity", International Journal of Urology, 2001, pp. 337-349, vol. 8.

Rozen et al., "Antiproliferative Action of Vitamin D-Related Compounds and Insulin-Like Growth Factor-Binding Protein 5 Accumulation", Journal of the National Cancer Institute, 1997, pp. 652-656, vol. 89, No. 9.

Wang et al., "Correlation of Glioma Cell Regression with Inhibition of Insulin-Like Growth Factor 1 and Insulin-Like Growth Factor-Binding Protein-2 Expression", Neuroendocrinology, 1997, pp. 203-211, vol. 66, No. 3.

Zangemeister-Wittke et al., "A Novel Bispecific Antisense Oligonucleotide Inhibiting Both bcl-2 and bcl-xL Expression Efficiently Induces Apoptosis in Tumor Cells", Clinical Cancer Research, 2000, pp. 2547-2555, vol. 6.

\* cited by examiner

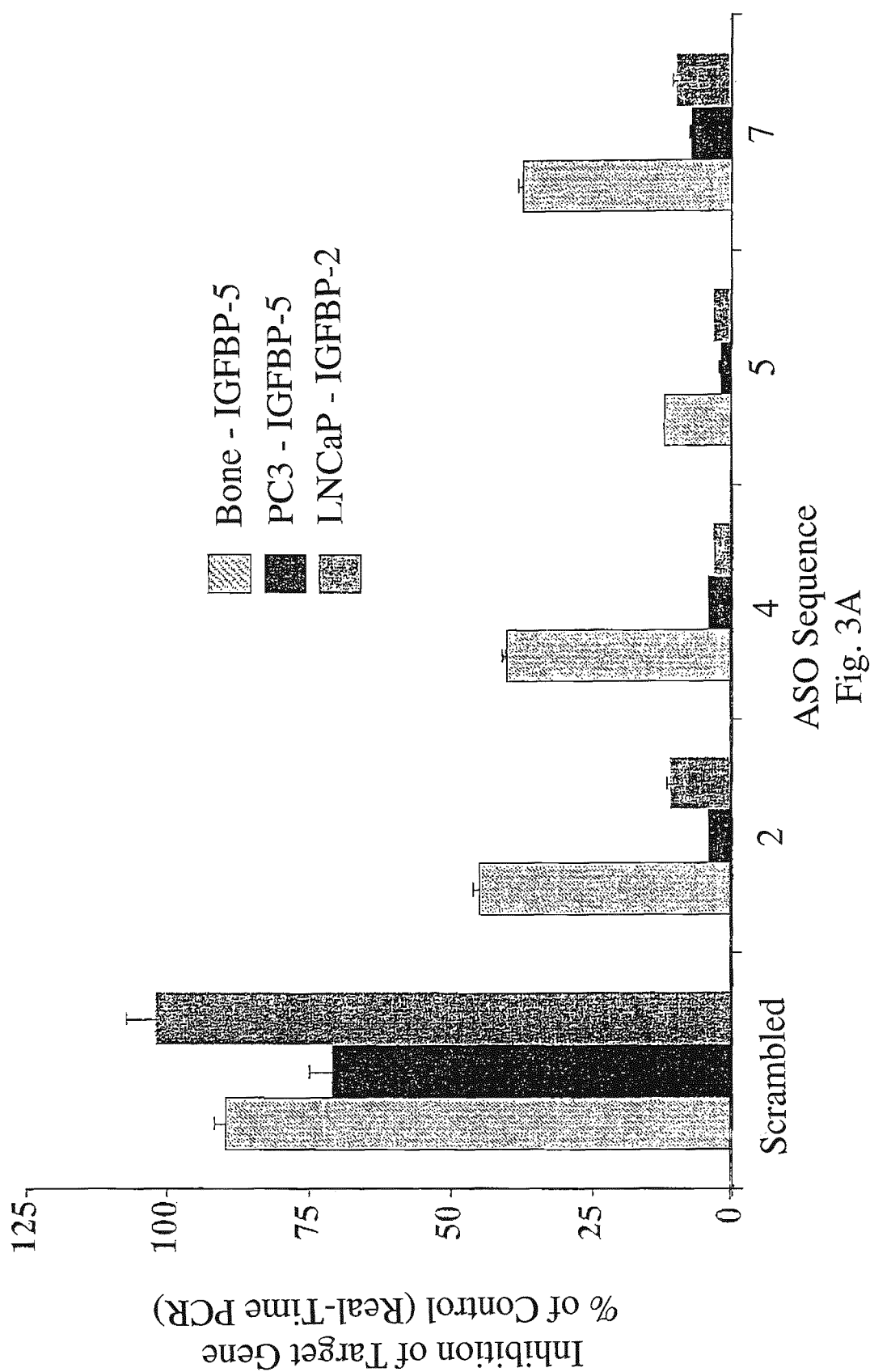

```
                         SEQUENCE LISTING

<160> NUMBER OF SEQ ID NOS: 7

<210> SEQ ID NO 1
<211> LENGTH: 17
<212> TYPE: DNA
<213> ORGANISM: human

<400> SEQUENCE: 1
ggtgtagacg ccgcacg                                              17

<210> SEQ ID NO 2
<211> LENGTH: 16
<212> TYPE: DNA
<213> ORGANISM: human

<400> SEQUENCE: 2
gcagcgcagc ccctgg                                               16

<210> SEQ ID NO 3
<211> LENGTH: 22
<212> TYPE: DNA
<213> ORGANISM: human

<400> SEQUENCE: 3
gcagcagccg cagcccggct cc                                        22

<210> SEQ ID NO 4
<211> LENGTH: 18
<212> TYPE: DNA
<213> ORGANISM: human

<400> SEQUENCE: 4
agccgcagcc cggctcct                                             18

<210> SEQ ID NO 5
<211> LENGTH: 20
<212> TYPE: DNA
<213> ORGANISM: human

<400> SEQUENCE: 5
cagcagccgc agcccggctc                                           20

<210> SEQ ID NO 6
<211> LENGTH: 20
<212> TYPE: DNA
<213> ORGANISM: human

<400> SEQUENCE: 6
gcagcagccg cagcccggct                                           20

<210> SEQ ID NO 7
<211> LENGTH: 20
<212> TYPE: DNA
<213> ORGANISM: human

<400> SEQUENCE: 7
agcagccgca gcccggctcc                                           20
```

BISPECIFIC ANTISENSE OLIGONUCLEOTIDES THAT INHIBIT IGFBP-2 AND IGFBP-5 AND METHODS OF USING SAME

This application claims the benefit of U.S. Provisional Application No. 60/350,046, filed Jan. 17, 2002, which is incorporated herein by reference.

BACKGROUND OF THE INVENTION

This present application relates to bispecific antisense oligonucleotides that inhibit IGFBP-2 and IGFBP-5 and methods of using same in the treatment of endocrine-regulated tumors (for example, breast, prostate, ovarian and colon cancers).

Prostate cancer is the most common cancer that affects men, and the second leading cause of cancer deaths in men in the Western world. Because prostate cancer is an androgen-sensitive tumor, androgen withdrawal, for example via castration, is utilized in some therapeutic regimens for patients with advanced prostate cancer. Androgen withdrawal leads to extensive apoptosis in the prostate tumor, and hence to a regression of the disease. However, castration-induced apoptosis is not complete, and a progression of surviving tumor cells to androgen-independence ultimately occurs. This progression is the main obstacle to improving survival and quality of life, and efforts have therefore been made to target androgen-independent cells. These efforts have focused on non-hormonal therapies targeted against androgen-independent tumor cells, however as of a 1998 report, no non-hormonal agent had improved survival. Oh et al., *J. Urol* 160: 1220-1229 (1998) Alternative approaches are therefore indicated.

Insulin-like growth factor (IGF)-I and are potent mitogens for many normal and malignant cells. Accumulating evidence suggests that IGFs play an important role in the pathophysiology of prostatic disease and breast cancer. Boudon et al., *J. Clin. Endocrin. Metab.* 81: 612-617 (1996); Angelloz-Nicoud et al., *Endocrinology* 136: 5485-5492 (1995); Nickerson et al., *Endocrinology* 139: 807-810 (1998); Figueroa et al., *J. Urol.* 159: 1379-1383 (1998).

The biological response to IGF's is regulated by various factors, including IGFBPs. To date, six IGFBPs have been identified whose function is believed to involve modulation of the biological actions of the IGFs through high affinity interactions. Rajaram et al., *Endocrin. Rev.* 18: 801-813 (1997). However, some evidence suggests biological activity for IGFBPs that are independent of IGFs, Id., Andress et al., *J. Biol. Chem.* 267: 22467-22472 (1992); Oh et al., *J. Biol. Chem.* 268: 14964-14971 (1993), and both stimulatory and inhibitory effects of IGFBPs on cell proliferation have been reported under various experimental conditions. Andress et al., supra; Elgin et al., *Proc. Nat'l. Acad. Sci.* (USA), 84, 3254-3258 (1987); Huynh et al., *J. Biol. Chem.* 271: 1016-1021 (1996); Damon et al., *Endocrinology* 139: 3456-3464 (1998). Thus, the precise function role of IGFBPs remains controversial. Because of this, while the reported results implicate IGF in prostate and breast cancer, they do not clearly suggest a therapeutic approach based upon this involvement.

PCT Publication WO 01/05435, which is incorporated herein by reference, describes a method for treating hormone-regulated tumors (for example, breast and prostatic tumors) in mammals, including humans, by administration of an antisense oligodeoxynucleotide which is complementary to a portion of the gene encoding IGFBP-5. PCT Publication No. WO 02/22642, which is incorporated herein by reference, describes a method are provided for the treatment of prostate and other endocrine tumors in mammals, including humans, by administration of an antisense oligodeoxynucleotide which is complementary to a portion of the gene encoding IGFBP-2.

The present invention utilizes bispecific antisense oligodeoxynucleotides targeted to both IBFBP-2 and IGFBP-5 as a treatment for endocrine-regulated cancers. Antisense oligodeoxynucleotides are chemically modified stretches of single-stranded DNA that are complementary to mRNA regions of a target gene, and thereby effectively inhibit gene expression by forming RNA/DNA duplexes. Figueroa, et al., *J. Urol.*, 159: 1379-1383 (1998). Phosphorothioate oligodeoxynucleotides are stabilized to resist nuclease digestion by substituting one of the nonbridging phosphoryl oxygen of DNA with a sulfur. Recently, several antisense oligodeoxynucleotides specifically targeted against genes involved in neoplastic progression have been evaluated both in vitro and in vivo, and demonstrated the efficacy of antisense strategy as potential therapeutic agents. Monia, et al. *Nature Med.* 2: 668-675 (1996.); Cucco, et al., *Cancer Res.* 56: 4332-4337 (1996); Ziegler, et al., *J. Natl. Cancer Inst.* 89: 1027-1036 (1997); Jansen, et al., *Nature Med.* 4: 232-234 (1998).

SUMMARY OF THE INVENTION

The present invention provides a method for treating endocrine-regulated tumors (for example, breast, prostate, ovarian and colon cancers) in mammals, including humans, by administration of a bispecific antisense oligodeoxynucleotide which is complementary to portions of both the gene encoding IGFBP-2 and the gene encoding IGFBP-5. The administration of such an oligodeoxynucleotide was shown to reduce levels of both IGFBP-2 and IGFBP-5 in PC3 and LNCaP cells, and the reduction of expression of the proteins has been previously shown to reduce proliferation of tumor cells, and also to delay the progression to androgen independence. Thus, in accordance with the invention we provide methods for treatment of prostate cancer in mammals, including humans, and for delaying the progression of prostate tumors to androgen independence comprising the step of administering to the mammal a therapeutically effective amount of a bispecific antisense oligodeoxynucleotide which is complementary to portions of both the nucleic acid sequence encoding IGFBP-2 and the nucleic acid sequence encoding IGFBP-5, and which hybridizes with such sequences to inhibit or otherwise reduce the expression of IGFBP-2 and IGFBP-5.

The application further provides bi-specific antisense sequences that can be used in the method of the invention.

BRIEF DESCRIPTION OF THE FIGURES

FIGS. 3A-E shows inhibition of IGFBP-2 and 5 in prostate cancer and bone cells using various antisense oligonucleotides.

DETAILED DESCRIPTION OF THE INVENTION

Figure 1A:
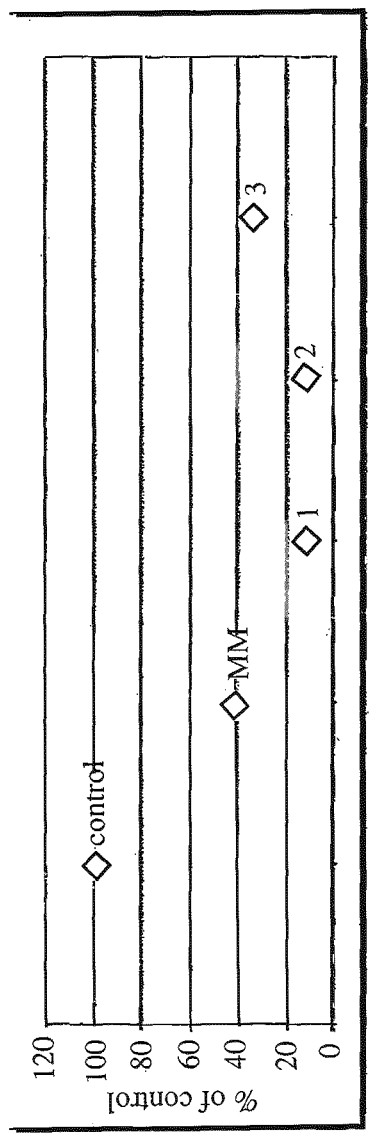
FIG. 1 the amount of IGBFP-2 and IGBFP-5 expression observed in LNCaP and PC3 cells, respectively, upon administration of the three bispecific antisense oligonucleotide, a mismatch control (MM), or no olignucleotide (control).

The present invention provides bispecific antisense oligonucleotides which consist essentially of a sequence of bases that is complementary to portions of both the gene encoding IGFBP-2 and the gene encoding IGFBP-5, and that is sufficient length to act as an inhibitor of the effective amount of IGFBP-2 and IGFBP-5 (in general at least 15 bases). As used in the specification and claims of this application, this language means that substantially all of the antisense oligonucleotide is complementary to a portion of each gene sequence. The invention does not, however, exclude minor modifications in sequence, such as the addition of one or two terminal bases, or single base substitutions which might depart from perfect complementarity but which still function as an inhibitor of the effective amount of IGFBP-2 and IGFBP-5.

The phrase "inhibitor of the effective amount" takes into account the fact that antisense oligonucleotides may function by different mechanisms. The effective amount of IGFBP-2 or IGFBP-5 is the amount that is present in a functional state in the cell. Reduction of this amount by administration of antisense oligonucleotides may occur through restricting production of the IGFBP (at the transcription or translation level) or by degrading the IGFBP at a rate faster than it is being produced. Further, it will be appreciated that the inhibition which is referred to is one which occurs when the IGFBP would otherwise be present if the antisense oligonucleotide had not been administered. As discussed below, not all cells that are potential therapeutic targets express both IGFBP-2 and IGFBP-5.

Specific antisense oligonucleotides according to the invention consist essentially of a series of bases as set forth in Seq. ID. No. 1 through 7. These sequences are set forth in Table 1.

TABLE 1

| Seq. ID NO. | Sequence |
|---|---|
| 1 | ggtgtagacgccgcacg |
| 2 | gcagcgcagccctgg |
| 3 | gcagcagccgcagcccggctcc |
| 4 | agccgcagcccggctcct |
| 5 | cagcagccgcagcccggctc |
| 6 | gcagcagccgcagcccggct |
| 7 | agcagccgcagcccggctcc |

The antisense oligonucleotides employed may be modified to increase the stability of the antisense oligonucleotide in vivo. For example, the antisense oligonucleotides may be employed as phosphorothioate derivatives (replacement of a non-bridging phosphoryl oxygen atom with a sulfur atom) which have increased resistance to nuclease digestion. Increased antisense oligonucleotide stability can also be achieved using molecules with 2-methoxyethyl (MOE) substituted backbones as described generally in U.S. Pat. No. 6,451,991 and U.S. patent application Ser. No. 10/080,794 which are incorporated herein by reference.

The compositions of the present invention can be used for treatment of endocrine-regulated tumors (for example, breast, prostate, ovarian and colon cancers) in mammals, including humans, by administration of a bispecific antisense oligonucleotide in accordance with the invention. Administration of antisense oligonucleotides can be carried out using the various mechanisms known in the art, including naked administration and administration in pharmaceutically acceptable carriers. For example, lipid carriers for antisense delivery are described in U.S. Pat. Nos. 5,855,911 and 5,417,978 which are incorporated herein by reference. In general, the antisense is administered by intravenous, intraperitoneal, subcutaneous or oral routes. Where the oligonucleotides are administered in a pharmaceutically acceptable carrier, the carrier is generally free from substances which produce toxic or other harmful reactions when administered to humans.

The amount of antisense oligonucleotide administered is one effective to reduce the effective amount of levels of IGFBP-2 and/or IGFBP-5 in the endocrine-regulated tumor cell of concern. As noted above, in the context of the present invention, applicants do not intend to be bound by any specific mechanism by which this reduction may occur, although it is noted that the reduction may occur as a result of reduced expression of IGFBP-2 and -5 if the antisense molecule interferes with translation of the mRNA, or via an RNase mediated mechanism. Furthermore, it will be appreciated that the appropriate therapeutic amount will vary both with the effectiveness of the specific antisense oligonucleotide employed, and with the nature of any carrier used. The determination of appropriate amounts for any given composition is within the skill in the art, through standard series of tests designed to assess appropriate therapeutic levels.

The method for treating endocrine-regulated cancer in accordance with the invention may further include administration of chemotherapy agents and/or additional antisense oligonucleotides directed at different targets. For example, conventional chemotherapy agents such as taxol (paclitaxel or docetaxel) and mitoxanthrone may be used. Similarly, combinations of the bispecific antisense oligonucleotide of the invention with other antisense sequences such as antisense Bcl-2 oligonucleotide, TRPM-2 (clusterin) oligonucleotide, IGFBP-2 or IGFBP-5 oligonucleotide may be used.

The effectiveness of the present invention is founded on solid theoretical and experimental bases. Activation of alternative growth factor pathways following androgen withdrawal is one mechanism mediating androgen independent (AI) progression in advanced prostate cancer. Insulin-like growth factor-I (IGF-I) activation is modulated by a family of insulin-like growth factor binding proteins (IGFBPs). Although IGFBP-2 and IGFBP-5 are among the most commonly over-expressed genes in hormone refractory prostate cancer, the functional significance of changes in IGF-I signaling during AI progression remain poorly defined. AI progression of prostate cancer leads to treatment resistance and ultimately culminates in the development of bone metastases, the most ominous sign of clinical progression in prostate cancer patients with advanced disease. This development usually precedes death by 12-18 months. The bone environment, particularly rich in IGFBP-5, has long been identified as an attractive "soil" for supporting prostate cancer metastasis. The crucial IGF-1 signaling components IGFBP-2 and IGFBP-5 may not only be key to AI progression but also to the site-specific metastasis of prostate cancer. In an attempt to address these issues, we characterized changes in IGFBP-2 and IGFBP-5 in prostate cancer models after androgen withdrawal and evaluated their functional significance in AI progression using gain-of-function and loss-of-function analyses.

IGFBP-2 mRNA and protein levels increase 2-3-fold after androgen withdrawal in LNCaP cells in vitro in LNCaP tumors during AI progression in vivo. Increased IGFBP-2 levels after castration were also identified using a human prostate tissue microarray of untreated and post-hormone therapy-treated prostatectomy specimen. LNCaP cell transfectants (LNBP-2) that stably over-expressed IGFBP-2 had a shorter cell doubling-time and a lower rate of apoptosis in the absence of androgens. Reporter assays demonstrated that this increased growth potential did not result from IGFBP-2-mediated transcription of androgen-response elements. In vivo, the LNBP-2 cell line formed significantly more tumors in castrate mice and progressed to androgen independence more rapidly compared with a control cell line. Antisense oligonucleotides targeting IGFBP-2 reduced IGFBP-2 mRNA and protein expression by >70% in a dose-dependent and sequence-specific manner. Antisense oligonucleotide-induced decreases in IGFBP-2 reduced LNCaP cell growth rates and increased apoptosis 3-fold. LNCaP tumor growth and serum PSA levels in mice treated with castration plus adjuvant IGFBP-2 antisense oligonucleotide s were significantly reduced compared to mismatch control oligonucleotides.

Similar findings were obtained with gain-of-function and loss-of-function analyses of IGFBP-5 in IGFBP-5 expressing prostate cancer models. The growth rates of IGFBP-5 transfected LNCaP cells were significantly faster compared to either the parental or vector-only transfected LNCaP cells in both the presence and absence of dihydrotestosterone. IGFBP-5-induced increases in LNCaP cell proliferation occurs through both IGF-I-dependent and -independent pathways, with corresponding increases in the cyclin D1 mRNA expression and the fraction of cells in S+G2/M phases of the cell cycle. Changes in Akt/protein kinase B (PKB), a downstream component of phosphatidylinositol 3'-kinase (PI3K) pathway, in the LNCaP sublines also paralleled changes in their growth rates. Although treatment with a PI3K inhibitor induced apoptosis in both control and IGFBP-5-overexpressing LNCaP cells, this PI3K inhibitor-induced apoptosis was prevented by exogenous IGF-I treatment only in IGFBP-5 transfectants, suggesting that IGFBP-5 overexpression can potentiate the antiapoptotic effects of IGF-I. Furthermore, tumor growth and serum PSA levels increased several fold faster in mice bearing IGFBP-5-transfected LNCaP tumors after castration despite having similar tumor incidence and tumor growth rates with controls when grown in intact mice before castration. These data suggest that IGFBP-5 overexpression in prostate cancer cells after castration is an adaptive cell survival mechanism that helps potentiate the antiapoptotic and mitogenic effects of IGF-I, thereby accelerating progression to androgen-independence through activation of the PI3K-Akt/PKB signaling pathway. Systemic administration of IGFBP-5 antisense oligonucleotides significantly delayed time to progression to androgen independence and inhibited growth of AI recurrent tumors. IGFBP-5 expression in human bone was confirmed.

Inhibiting IGFBP-2 and IGFBP-5 expression using targeted antisense technologies provides a treatment platform to delay AI progression and bone metastasis in prostate cancer patients and patients with other malignancies expressing these key regulators of IGF-1 signaling. By targeting both IGFBP-2 and IGFBP-5 simultaneously with a single antisense oligonucleotide the complications associated with use of a cocktail of antisense oligonucleotides targeting either of these compounds separately are avoided.

The application is further described in the following non-limiting examples.

EXAMPLE 1

LNCaP cells were treated with treated with 500 nM concentrations of antisense oligonucleotides of Seq. ID Nos. 1, 2 or 3 or a mismatch control. Levels of IGFBP-2 were measured. The result are summarized in FIG. 1A.

Figure 1B:
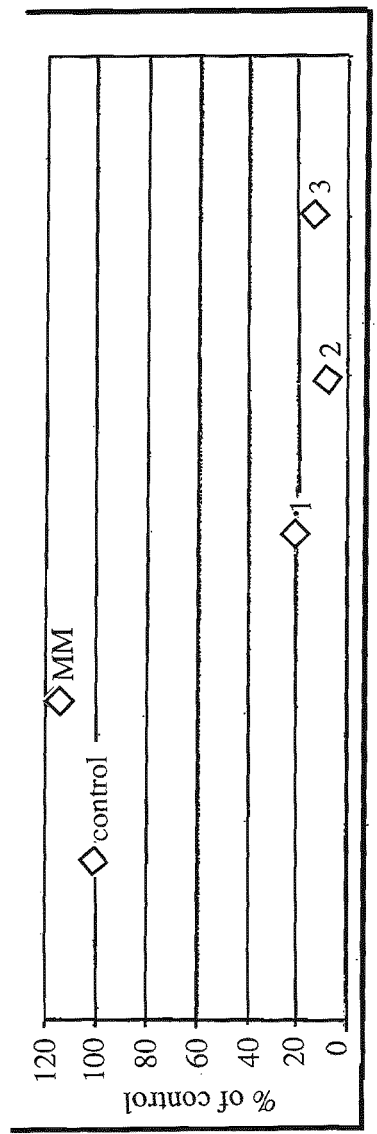

PC3 cells were treated with treated with 500 nM concentrations of antisense oligonucleotides of Seq. ID Nos. 1, 2 or 3 or a mismatch control. Levels of IGFBP-5 were measured. The result are summarized in FIG. 1B.

EXAMPLE 2

Figure 2:
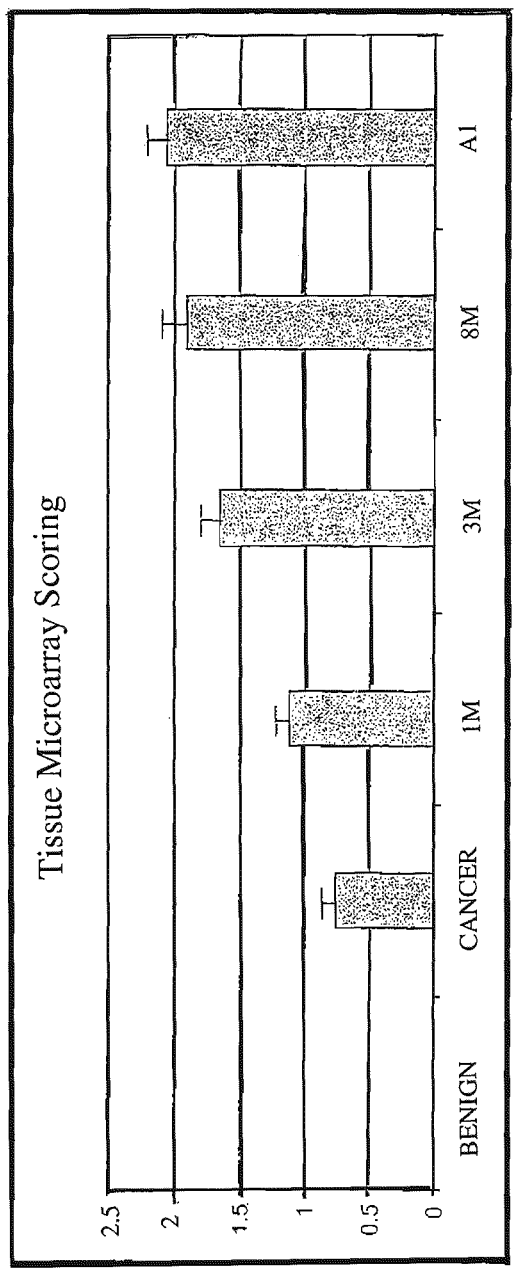
FIG. 2 shows the increase in IGFBP-2 expression in prostate cancer cells during progression to androgen independence.

Samples of human prostate cancer cells were sectioned and immuno-stained to detect IGFBP-2. Tissue microarray scoring showed expression of IGFBP-2 was essentially absent in benign, non-cancerous tissues but increased with time to highest levels after androgen independent was achieved. (FIG. 2)

EXAMPLE 3

Osseous metastases of human prostate cancer was evaluated in 15 specimens. Human prostate cancer expressed IGFBP-2 in very high levels, but also expressed IGFBP-5. Human bone osteocytes expressed high levels of IGFBP-5 and lower levels of IGFBP-2.

EXAMPLE 4

Figure 3B:
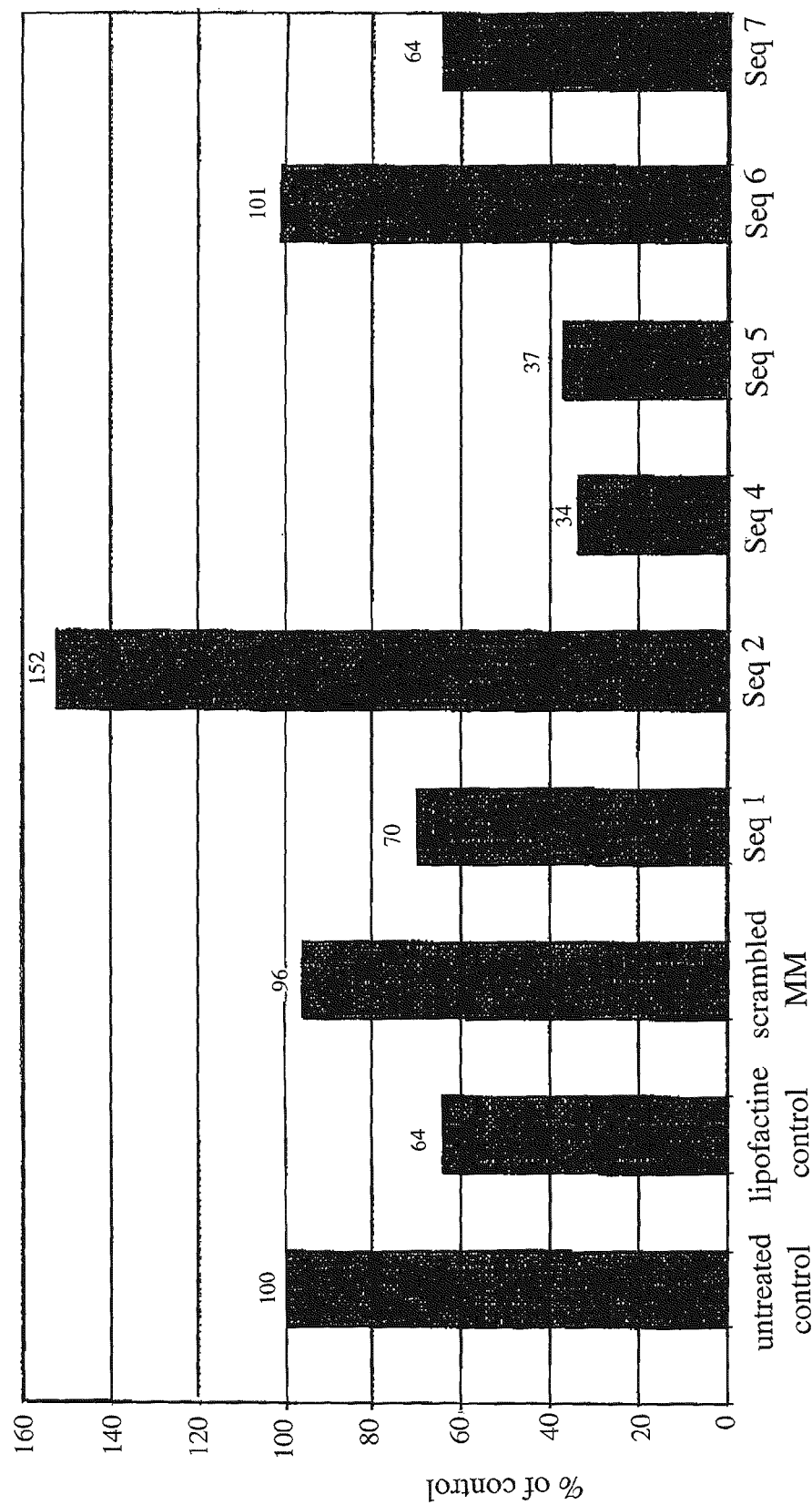
Figure 3C:
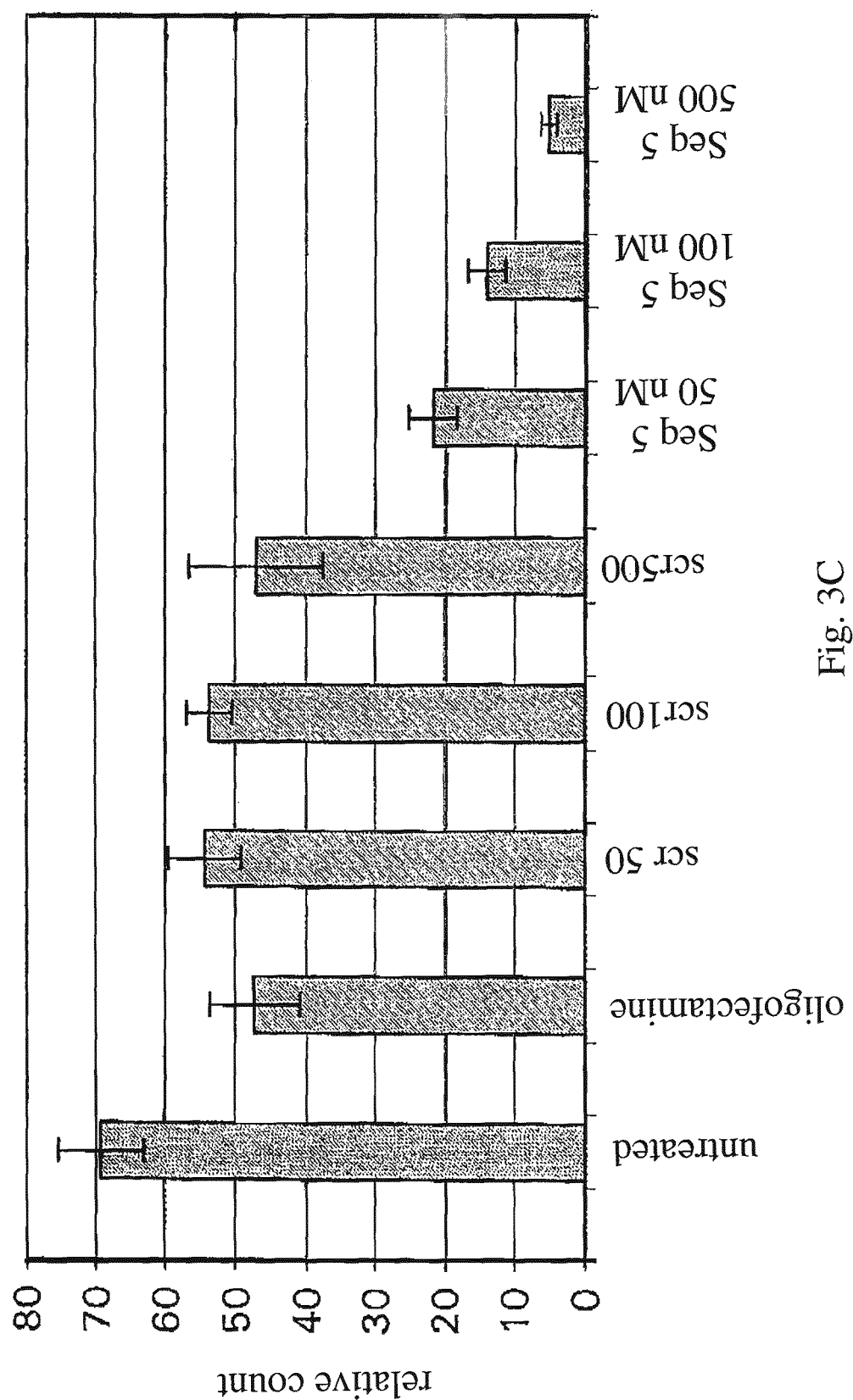
Figure 3D:
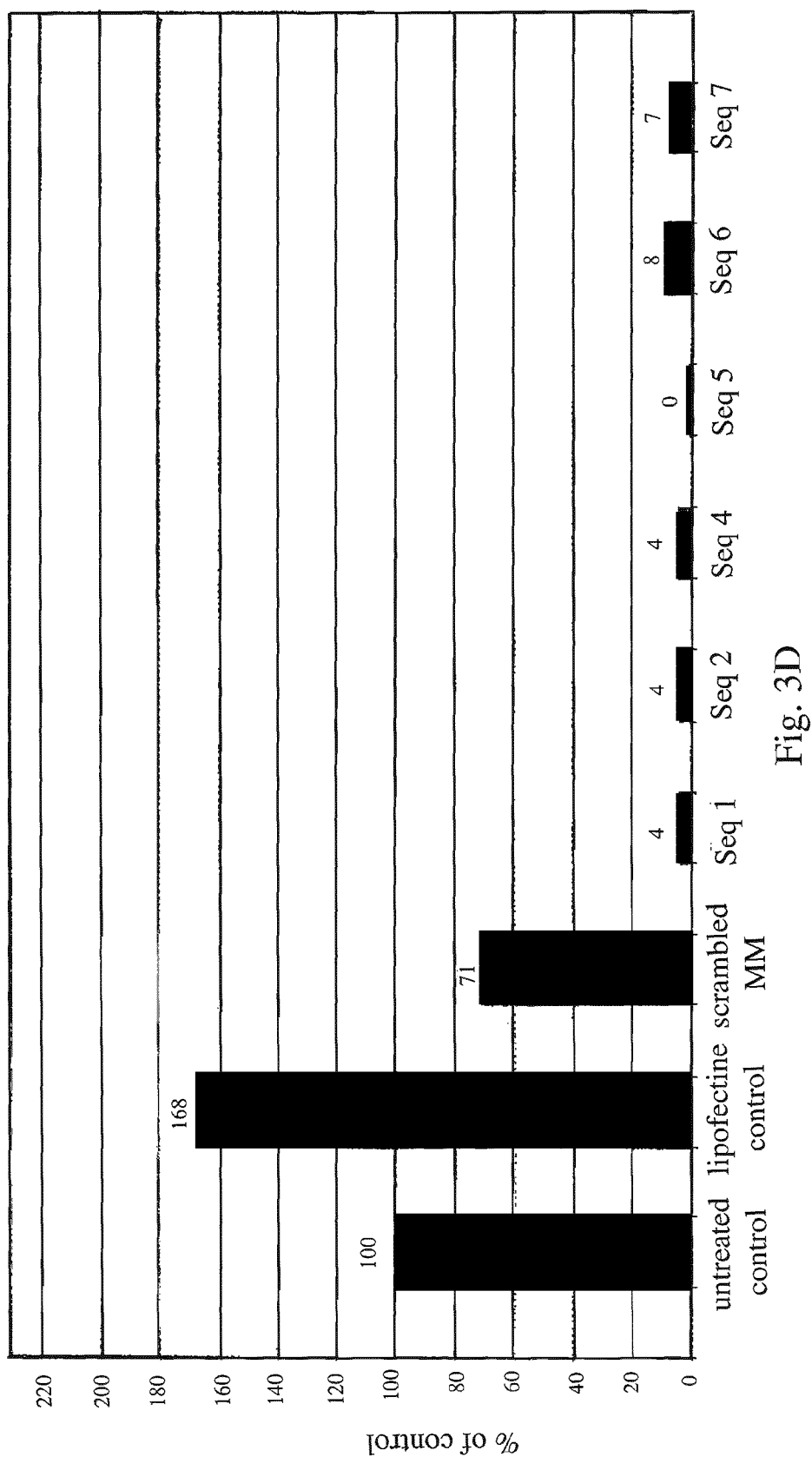
Figure 3E:
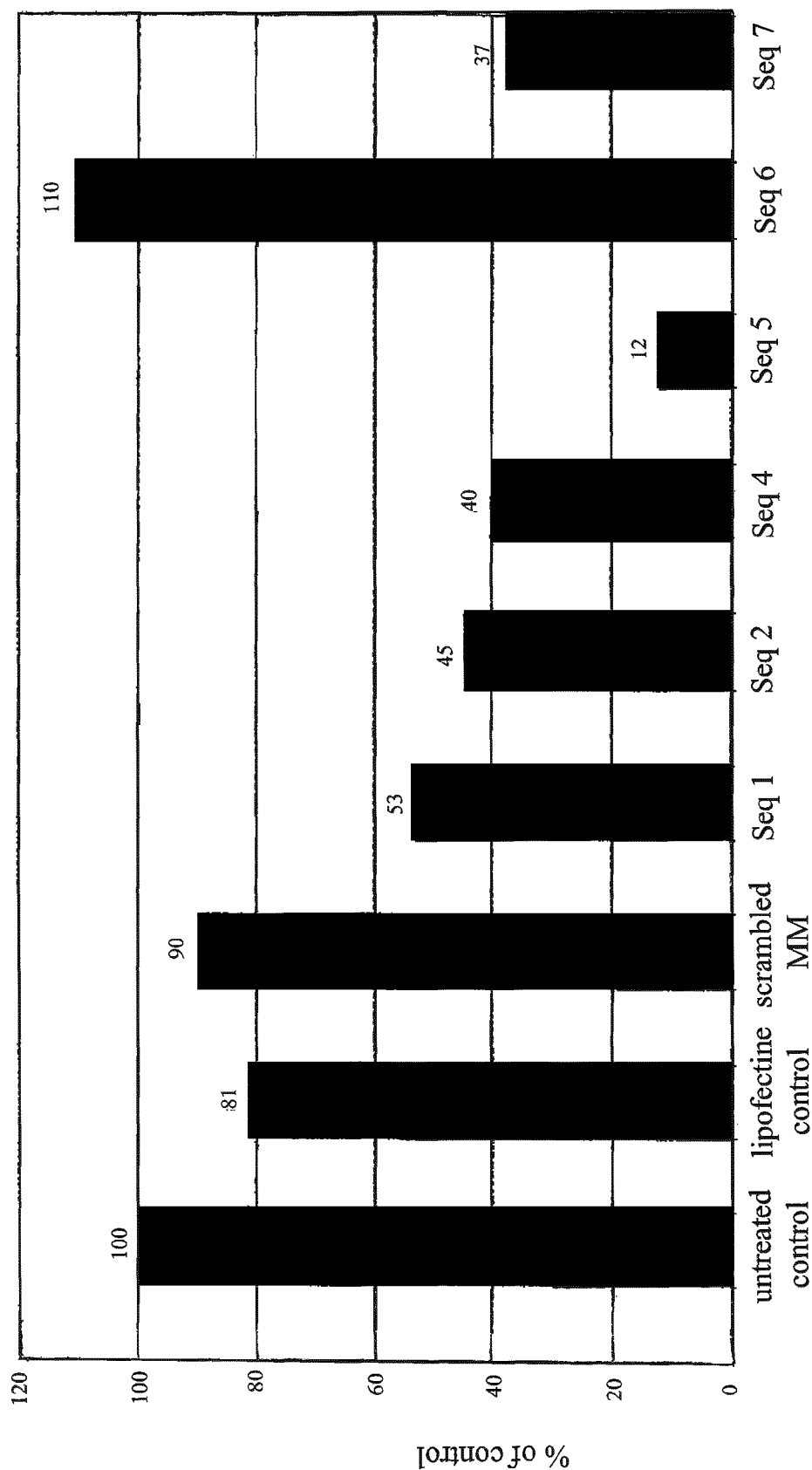

Bispecific antisense oligonucleotides were used to treat PC3, LNCaP and bone cells at concentration of 500 nm, and the amount of inhibition of IGFBP-2 or IGFBP-5 was measured using real time PCR. Oligonucleotides of Seq. ID Nos. 2, 4, 5 and 7 were tested, and all were effective to reduce the detected amount of the IGFBP measured. (FIG. 3A) Reductions of up to 70% in IGFBP-2 levels were also observed in A549 lung cells using 500 nM of Seq. ID Nos. 4 and 5. (FIG. 3B) Seq. ID No. 4 (500 nM) was also shown to be effective to inhibit cell growth of LNCaP cells and reduce the cell number by more than 90%. (FIG. 3C) FIGS. 3D and E respectively show results for inhibition of IGFBP-5 levels in PC3 cells with 500 nM of Seq ID Nos. 1, 2, 4 5, 6 and 7; and inhibition of IGBFP-5 levels in human fetal bone fobroblast cells with 500 nM of Seq. ID Nos. 1, 2, 4, 5, 6 and 7.

EXAMPLE 5

Figure 6:
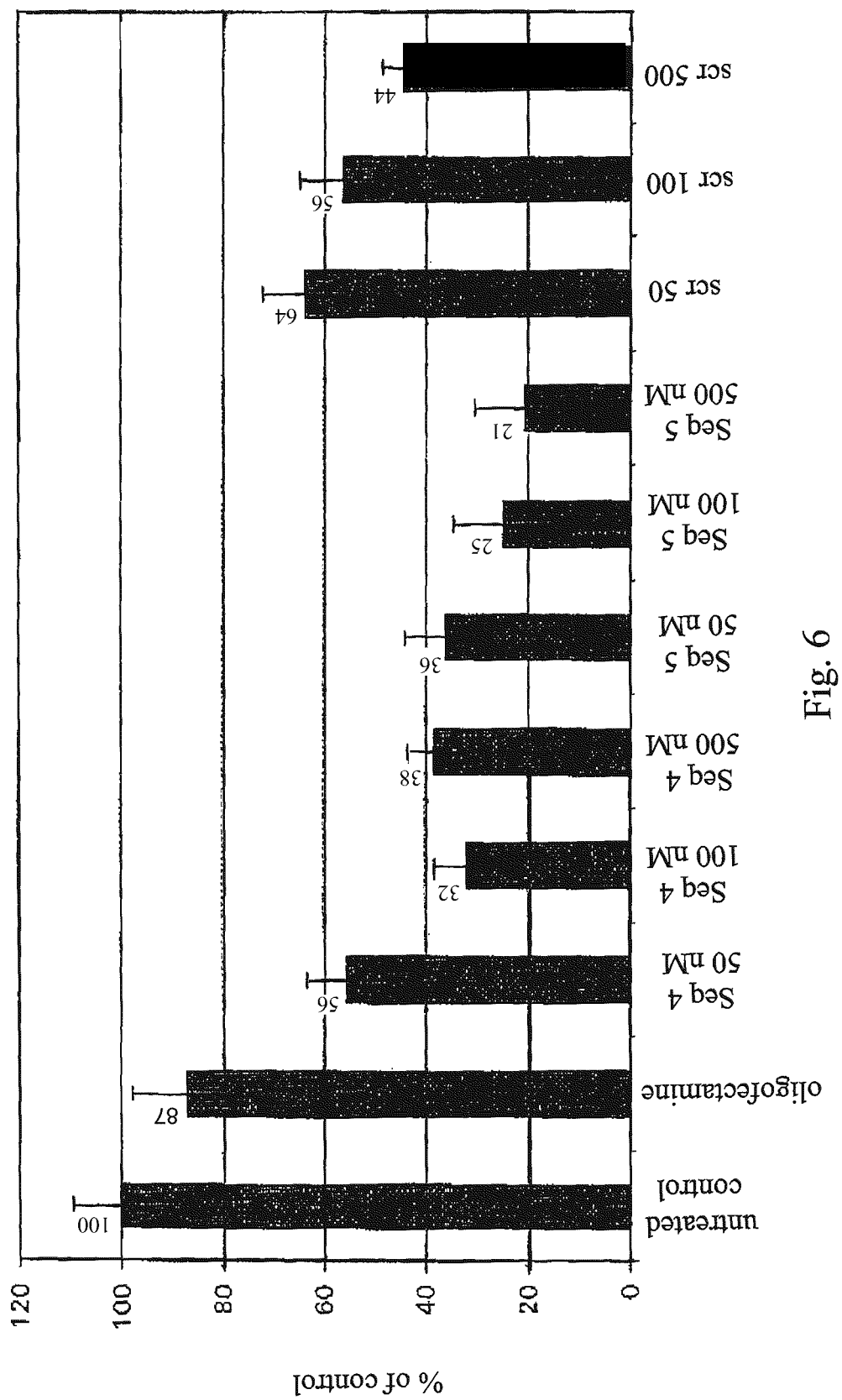
FIG. 6 shows results of real time PCR measurement of IGFBP-5 in MSF human fetal fibroblast cells after antisense treatment.

Real time PCR was used to measure the amount IGFBP-5 in MSF human fetal fibroblast cells after treatment with antisense oligonucleotide and LIPOFECTIN (4 µg/ml). Cells were plated in vitro and treated with a four-hour pulse of 500 nM oligonucleotide followed by a 20 hour period in normal medium plus 5% serum. A second four-hour pulse was repeated on day 2 and the cells were counted on day 3. The most active antisense oligonucleotides were Seq. ID Nos. 4 and 5. (FIG. 6)

EXAMPLE 6

Figure 4:
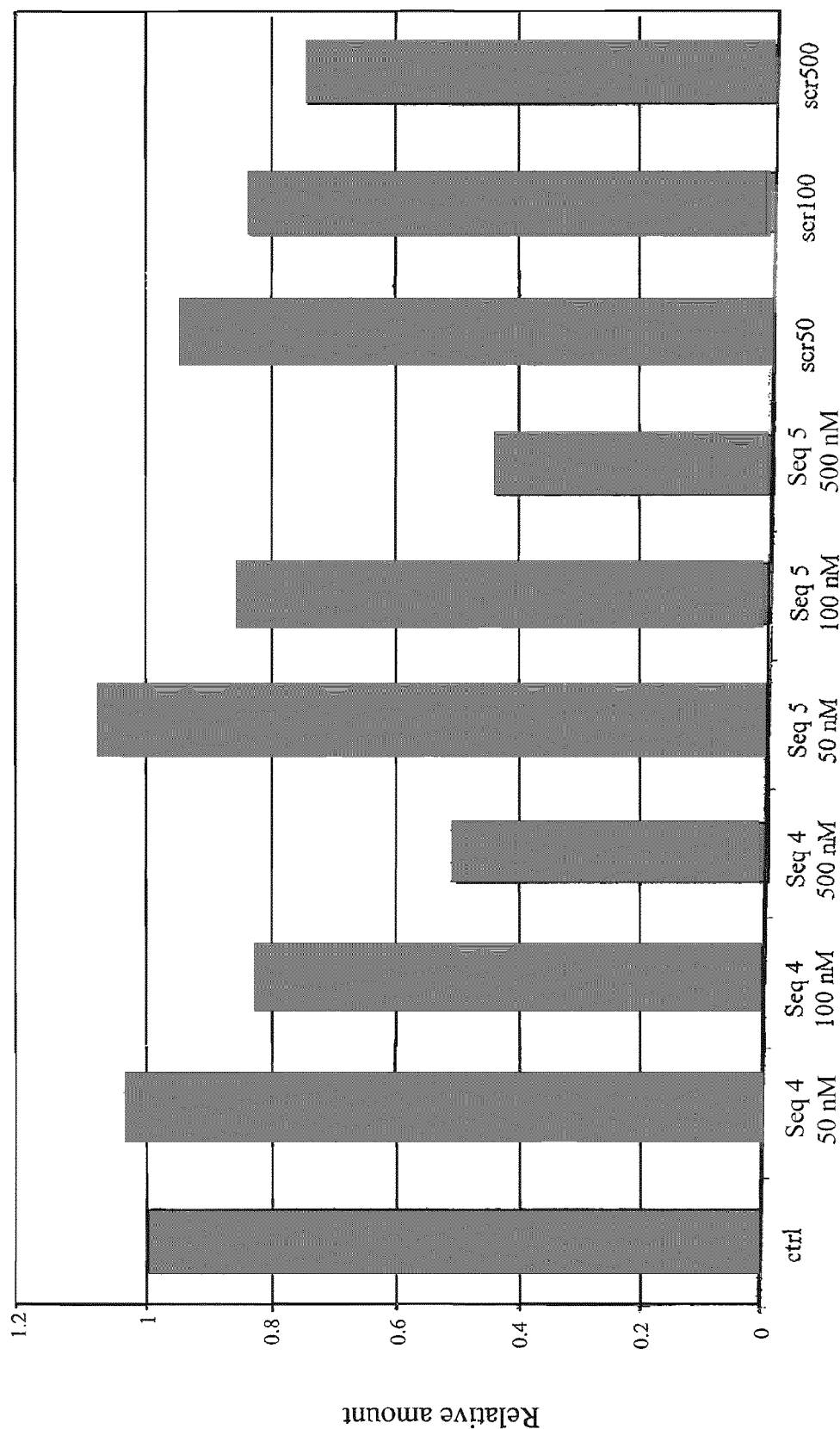
FIGS. 4 and 5 show real time PCR results for levels of IGFBP-2 and IGFBP-5 in RT4 bladder cancer cells after treatment with antisense oligonucleotides of the invention.
Figure 5:
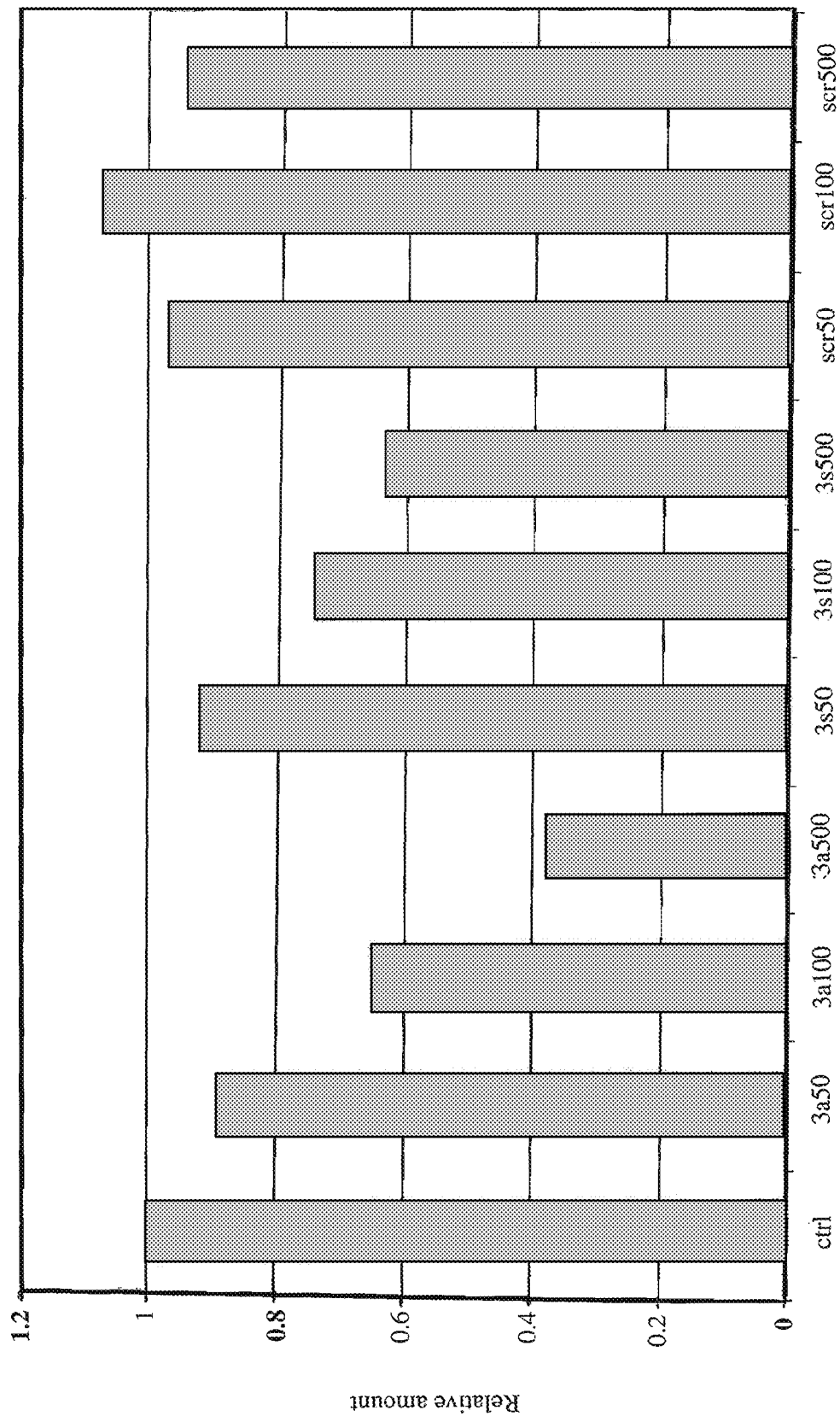

Real time PCR was used to evaluate the amounts of IGFBP-2 and IGFBP-5 in human bladder cancer (RT4) following treatment with varying amounts of antisense oligonucleotides (Seq. ID Nos. 4 and 5) and 4 µg/ml LIPOFECTIN. As shown in FIGS. 4 and 5, a dose dependent response was observed to both antisense oligonucleotides at concentrations ranging from 50 to 500 nM.

EXAMPLE 7

Figure 7:
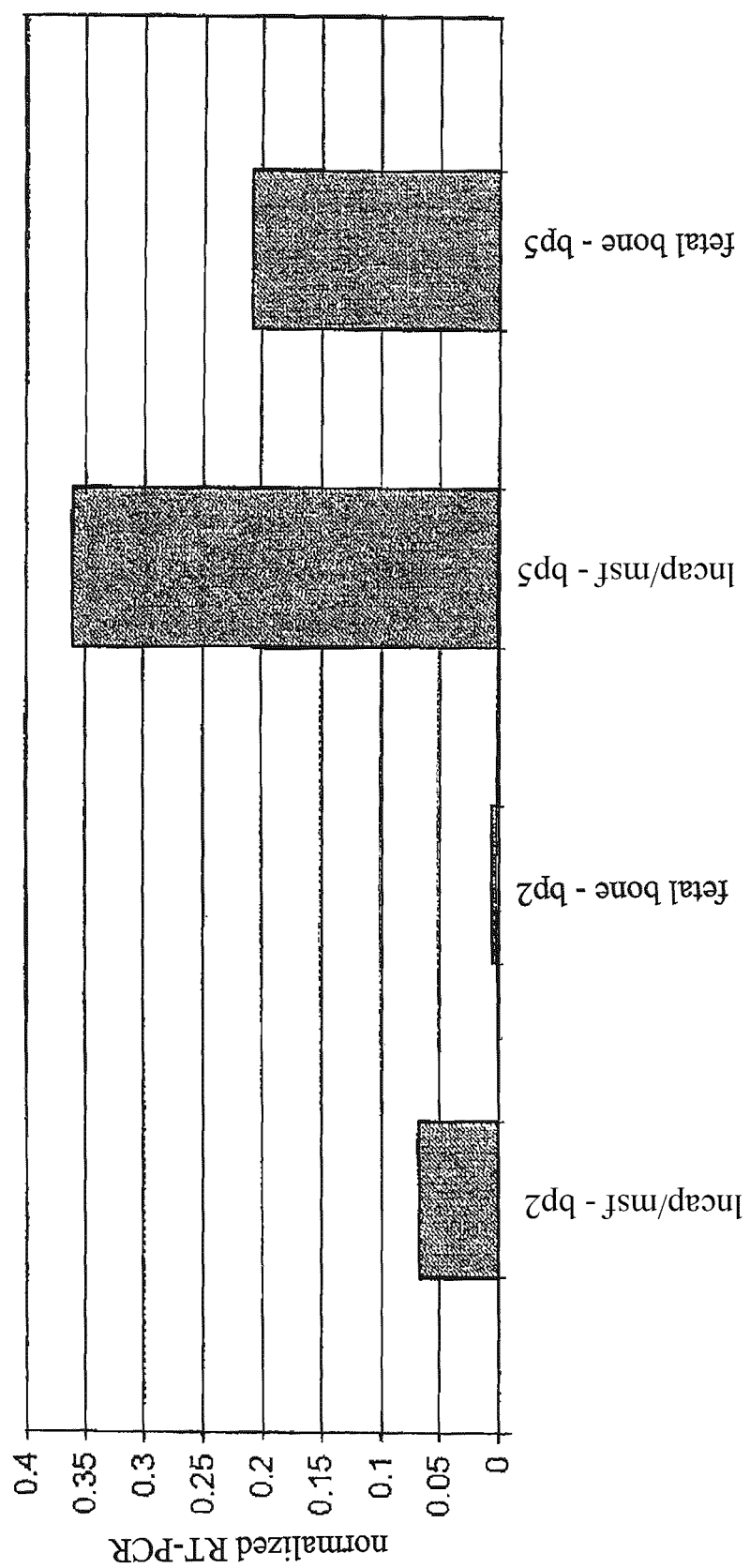
FIG. 7 shows the results of real time PCR measurements of IGFBP-2 and IGFBP-5 LNCaP/msf in mixed tumors and in intact fetal bone fragments

Real time PCR was used to measure IGFBP-2 and IGFBP-5 in LNCaP/msf mixed tumors and in intact fetal bone fragments. The results are shown in FIG. 7.

The invention claimed is:

1. A bispecific antisense oligodeoxynucleotide consisting of Seq. ID No. 5, wherein the oligodeoxynucleotide is modified to enhance in vivo stability.

2. The oligodeoxynucleotide of claim 1, wherein the oligodeoxynucleotide is a phosphorothioate derivative.

3. The oligodeoxynucleotide of claim 1, wherein the oligodeoxynucleotide has 2'-O-methoxyethyl substitutions on the backbone.

4. A pharmaceutical composition comprising a bispecific antisense oligodeoxynucleotide and a pharmaceutically acceptable carrier, wherein the oligodeoxynucleotide consists of Seq ID No. 5 modified to enhance in vivo stability.

5. The composition of claim 4, wherein the oligodeoxynucleotide is a phosphorothioate derivative.

6. The composition of claim 5, wherein the carrier is a carrier acceptable for intravenous, intraperitoneal, subcutaneous or oral administration.

7. The composition of claim 4, wherein the oligodeoxynucleotide has 2'-O-methoxyethyl substitutions on the backbone.

8. The composition of claim 7, wherein the carrier is a carrier acceptable for intravenous, intraperitoneal, subcutaneous or oral administration.

9. The composition of claim 4, wherein the carrier is a carrier acceptable for intravenous, intraperitoneal, subcutaneous or oral administration.

* * * * *